(12) United States Patent
Elbabaa et al.

(10) Patent No.: US 11,771,470 B1
(45) Date of Patent: Oct. 3, 2023

(54) AFFIXATION DEVICE FOR SECURING BONE FLAP

(71) Applicant: ORLANDO HEALTH, INC., Orlando, FL (US)

(72) Inventors: Samer K. Elbabaa, Orlando, FL (US); Michael J. Schmidt, Orlando, FL (US)

(73) Assignee: ORLANDO HEALTH, INC., Orlando, FL (US)

( * ) Notice: Subject to any disclaimer, the term of this patent is extended or adjusted under 35 U.S.C. 154(b) by 0 days.

(21) Appl. No.: 18/062,763

(22) Filed: Dec. 7, 2022

(51) Int. Cl.
*A61B 17/68* (2006.01)

(52) U.S. Cl.
CPC .................................. *A61B 17/688* (2013.01)

(58) Field of Classification Search
CPC .... A61B 17/688; A61B 17/80; A61B 17/8085
See application file for complete search history.

(56) References Cited

U.S. PATENT DOCUMENTS

| | | | |
|---|---|---|---|
| 6,168,596 B1 | 1/2001 | Wellisz et al. | |
| 6,572,623 B1 | 6/2003 | Birchall, Jr. et al. | |
| 8,241,336 B2 | 8/2012 | Ralph et al. | |
| 8,343,225 B2 | 1/2013 | Linares | |
| 9,017,406 B2 | 4/2015 | Seiler | |
| 9,271,773 B2 * | 3/2016 | Hwa | A61B 17/809 |
| 9,545,276 B2 * | 1/2017 | Buchanan | A61B 17/8061 |
| 9,592,124 B2 | 3/2017 | Joganic | |
| 10,307,192 B2 * | 6/2019 | Schlatterer | A61B 17/8061 |
| 10,835,379 B2 | 11/2020 | Gordon et al. | |
| 10,864,027 B2 * | 12/2020 | Schlatterer | A61B 17/8066 |
| 10,893,896 B2 | 1/2021 | Howard et al. | |
| 11,426,266 B2 | 8/2022 | Mathisen et al. | |
| 11,464,553 B2 * | 10/2022 | Schlatterer | A61B 17/8061 |
| 2006/0241609 A1 * | 10/2006 | Myerson | A61B 17/8061 606/280 |
| 2009/0076617 A1 * | 3/2009 | Ralph | A61B 17/688 623/17.19 |
| 2010/0094428 A1 * | 4/2010 | Ralph | A61B 17/688 606/280 |
| 2010/0256687 A1 * | 10/2010 | Neufeld | A61B 17/8061 606/280 |
| 2012/0165878 A1 * | 6/2012 | Hwa | A61B 17/809 606/280 |
| 2014/0277176 A1 * | 9/2014 | Buchanan | A61B 17/8057 606/280 |
| 2014/0358238 A1 | 12/2014 | Teoh et al. | |
| 2018/0110551 A1 * | 4/2018 | Schlatterer | A61B 17/8066 |
| 2019/0201063 A1 * | 7/2019 | Schlatterer | A61B 17/8066 |
| 2021/0045787 A1 * | 2/2021 | Schlatterer | A61B 17/809 |

FOREIGN PATENT DOCUMENTS

WO    WO-2010057148 A2 *    5/2010    ......... A61B 17/7044

\* cited by examiner

*Primary Examiner* — Eric S Gibson
(74) *Attorney, Agent, or Firm* — Crowell & Moring LLP

(57) ABSTRACT

An affixation device for a human skull may include a base plate that has an outer area for securing to the skull and an inner area for securing to a bone flap removed from the skull. The affixation device may also have at least one spacer located between the outer area and the inner area, where the at least one spacer extends from a first surface of the base plate, where the first surface facing the skull when the fixation device is in an installed state, and where the at least one spacer is configured to extend between the bone flap and the skull in the installed state.

18 Claims, 7 Drawing Sheets

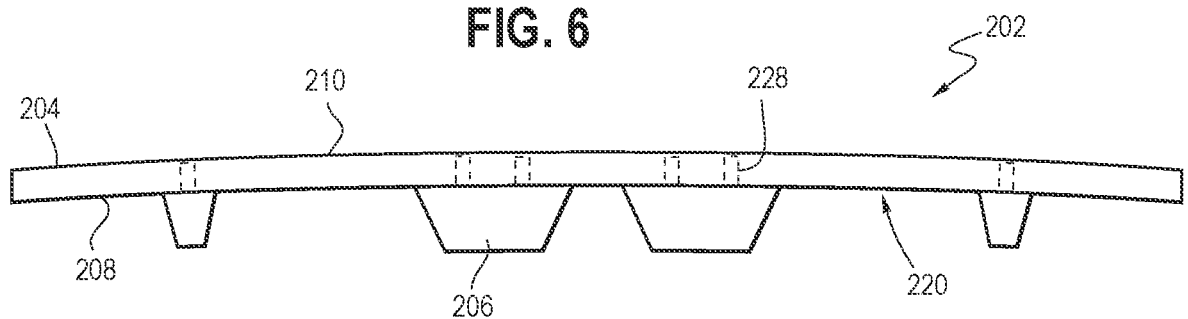
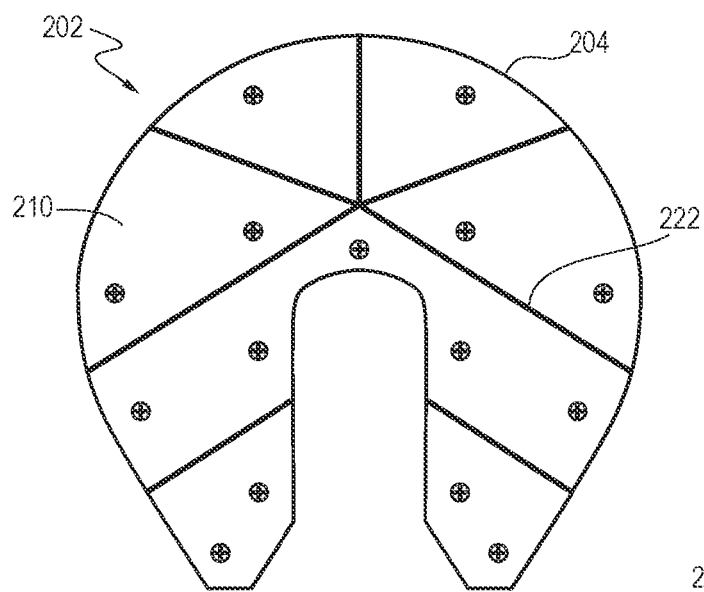
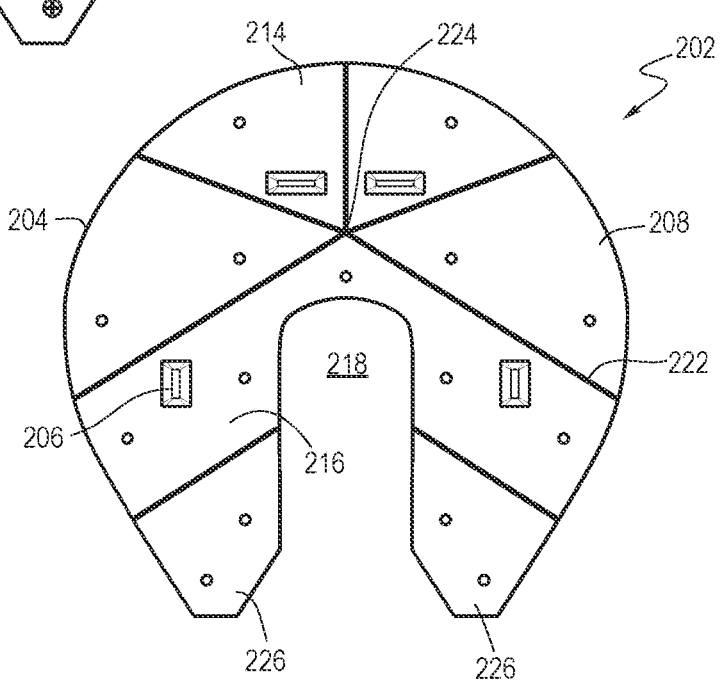

AFFIXATION DEVICE FOR SECURING BONE FLAP

TECHNICAL FIELD

The present disclosure relates to an affixation device for securing a surgically-removed bone flap to surrounding bone within a patient body.

BACKGROUND

The posterior fossa, a small space in the skull near the brainstem and cerebellum, is the most common site for brain tumors in children. Removal of such tumors often involves surgical intervention, where a portion of the skull must be removed to reach the tumor. While tumor removal is often successful, replacing the removed skull portion (hereafter the "bone flap") has proven difficult in practice. This procedure usually requires the use of commercially-available plates and screws, which have a high failure rate due to the low tensile strength of a young child's skull (often only 2-3 mm thick in infants). Standard, commercially-available strips or plates of metal are also difficult to secure to the child's skull since the posterior fossa has an irregular shape that varies between patients.

The present disclosure presents an affixation device for securing a bone flap to surrounding bone tissue that overcomes existing shortcomings in the field.

BRIEF DESCRIPTION OF THE DRAWINGS

The embodiments discussed herein may be better understood with reference to the following drawings and description. Certain features shown in the figures are not necessarily to scale. Moreover, in the figures, like-referenced numerals designate corresponding parts throughout the different views.

FIG. 6 is an illustration showing a view of an affixation device having a concave surface that corresponds to a convex surface of a skull in accordance with certain aspects of the present disclosure.

FIG. 7 is an illustration showing a side of the affixation device of FIG. 6 that faces away from the patient.

FIG. 8 is an illustration showing a side of the affixation device of FIGS. 6-7 that faces towards the patient and engages the patient's skull in accordance with certain aspects of the present disclosure.

DETAILED DESCRIPTION

Figure 1:
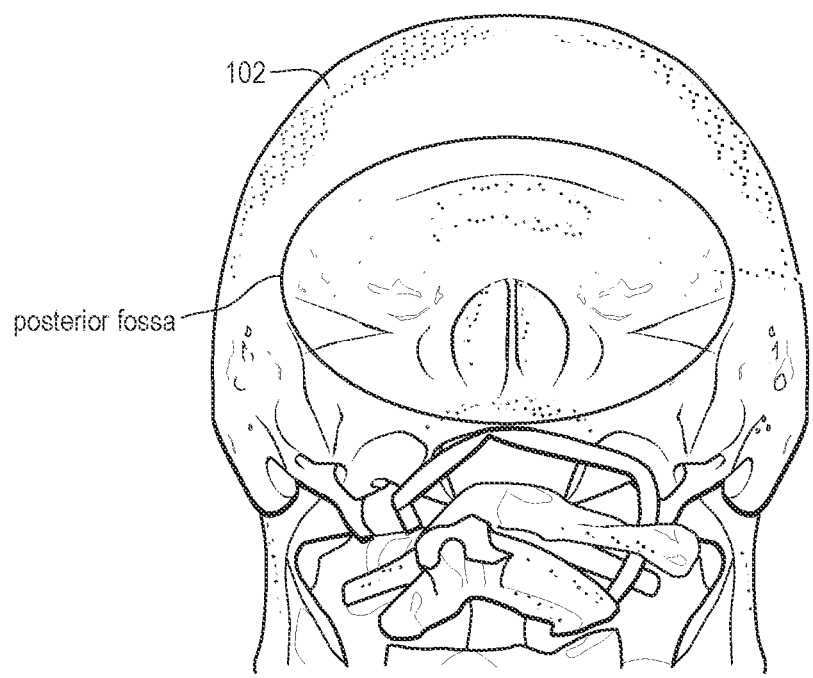
FIG. 1 is an illustration showing a posterior fossa of an infant patient.
Figure 2:
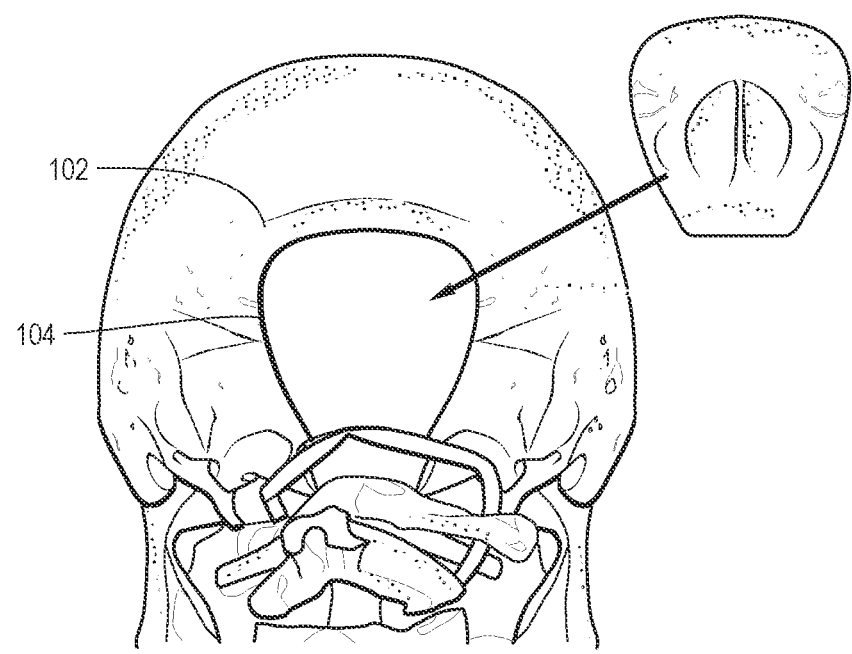
FIG. 2 is an illustration showing a bone flap that has been surgically removed from the posterior fossa of the infant patient such that a tumor may be removed from the brain.
Figure 3:
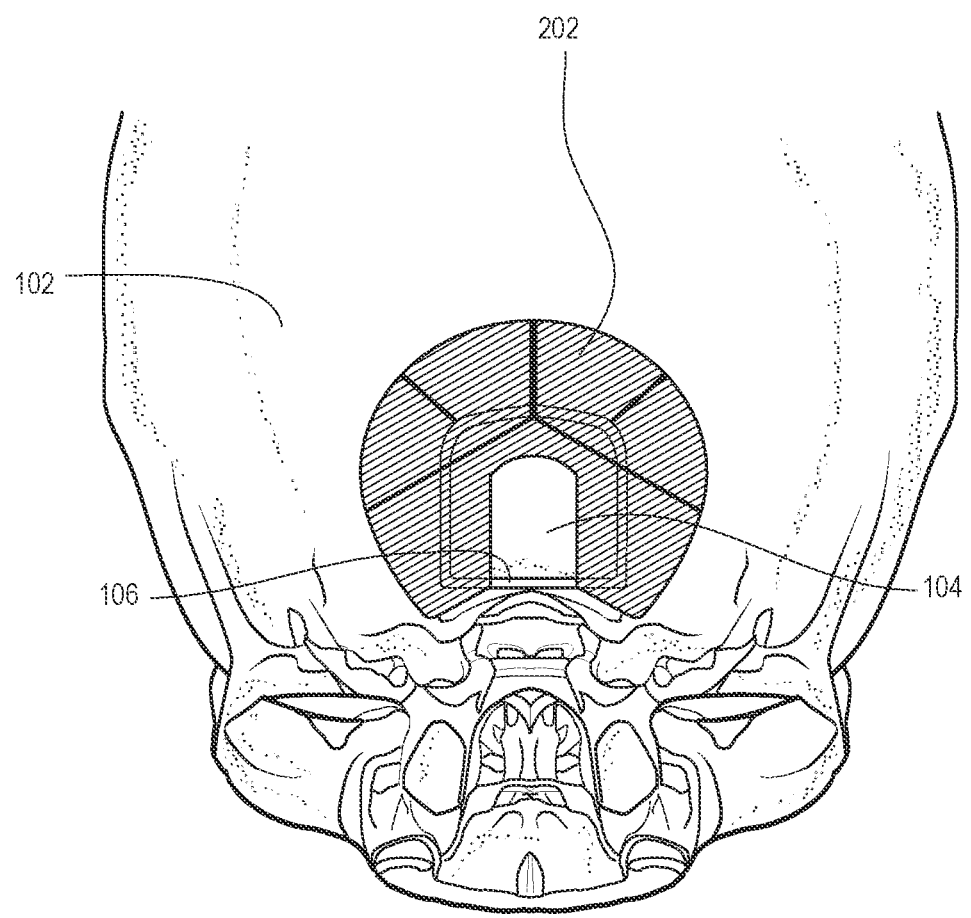
FIG. 3 is an illustration showing a first view of an affixation device for securing the bone flap to the skull in accordance with certain aspects of the present disclosure.
Figure 4:
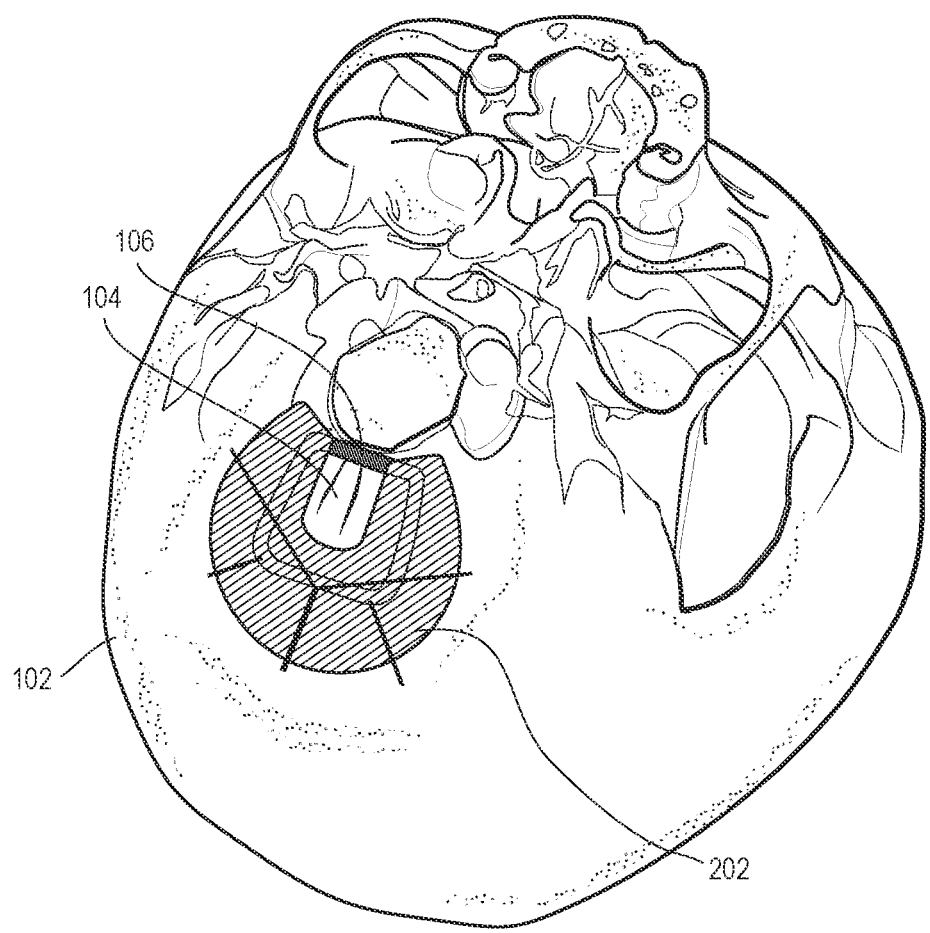
FIG. 4 is an illustration showing a second view of the affixation device for securing the bone flap to the skull in accordance with certain aspects of the present disclosure.
Figure 5:
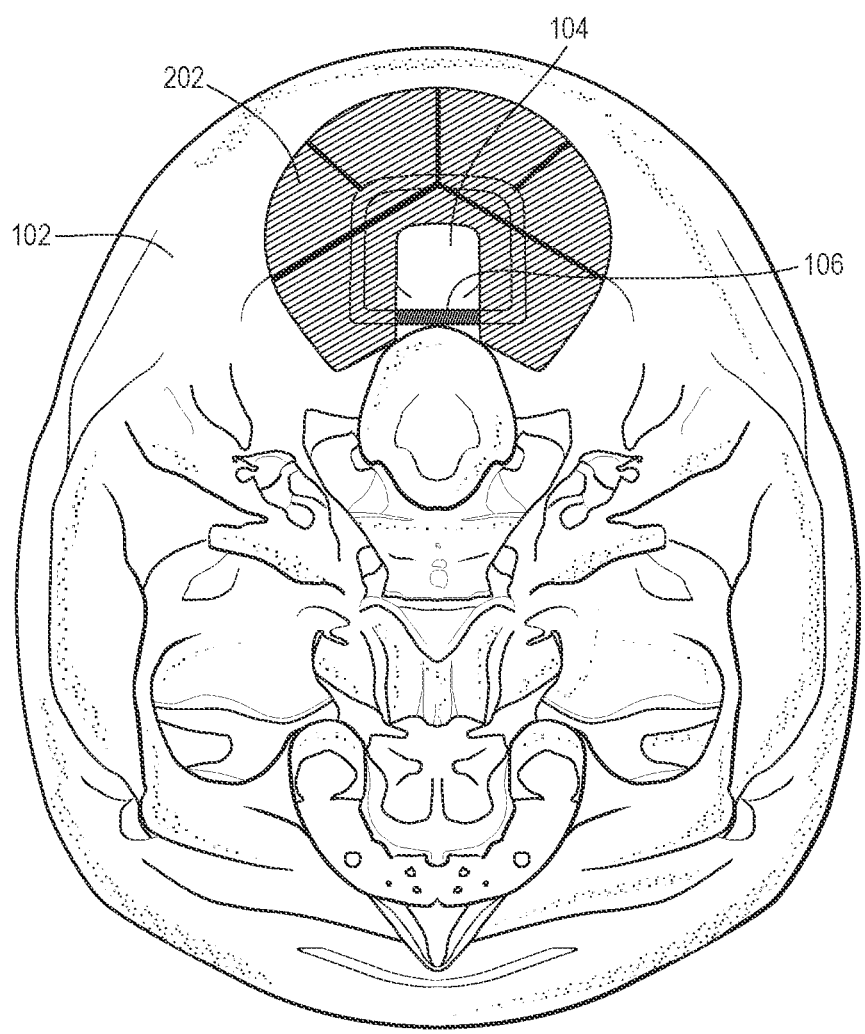
FIG. 5 is an illustration showing a third view of the affixation device for securing the bone flap to the skull in accordance with certain aspects of the present disclosure.

FIG. 1 identifies the posterior fossa of a human patient, which is a common site for the development of brain tumors (and the most common site in young children). To reach these tumors for surgical removal, a bone flap 104, shown in FIG. 2, must be removed from the surrounding skull 102. As discussed in the background above, replacement of the bone flap 104 has proven difficult in practice. This disclosure presents an affixation device that improves securement of the bone flap 104, reduces the failure rate, and lessens the difficulty of the surgery. Notably, while the affixation device described herein is particularly tailored for securing a bone flap near the posterior fossa, the invention also may be utilized for other areas of the skull and/or other areas where bone flaps may be removed and replaced within a human or animal body.

FIGS. 3-11 show certain embodiment(s) of a fixation device 202 for a human skull 102, which may be used to anchor the bone flap in place after surgery. The fixation device 202 may be permanent or temporary, and (as discussed below) may eventually degrade via cellular activity in the body's environment via use of a resorbable material.

The fixation device 202 may generally include a base plate 204 and one or more spacers 206. The base plate 204 may generally function to directly secure the skull 102 and also the bone flap 104, meaning the base plate 204 may be considered the primary split for immobilizing the bone flap 104 relative to the skull 102. A first side 208 of the base plate 204 may generally face the skull 102, and a second side 210 of the base plate 204 may generally face away from the skull 102. As discussed in more detail below, the size and shape of the base plate 204 may be selected for a particular patient or procedure. Thus, it is contemplated that prior to the initiation of the surgery, several base plates of different sizes and/or shapes may be available to the surgeon. Optionally, cutting tools and/or other tools may be available for further tailoring of the base plate 204.

To facilitate securement of the base plate 204 to the skull 102 and the bone flap 104, the base plate 204 may include one or more screw openings 212 for receiving a bone screw, although such screw openings are optional. For example, the screw openings 212 in the outer perimeter area 214 may generally receive screws that engage the skull, and the screw openings 212 of the inner perimeter area 216 may receive screws that generally engage the bone flap 104. Notably, the screw openings 212 are optional (particularly when screws may simply penetrate the base plate 204 without pre-formed openings). Also, using bone screws is one of many contemplated methods for securing the base plate 204 to the underlying bone and is included only as an exemplary example.

In certain embodiments, the base plate 204 may be wholly or partially formed with one or more bioresorbable materials, hereafter "resorbable materials," many of which are known in the art. Without limitation, certain examples include resorbable polymers such as poly(lactic acid) ("PLA") and poly(glycolic acid) ("PGA"), and ceramics such as hydroxyapatite, tricalcium phosphate, and calcium carbonate.

The base plate 204 may have any suitable shape. In the depicted embodiment, the base plate 204 generally has a U-shape with an outer perimeter area 214 and an inner perimeter area 216, the inner perimeter area 216 surrounding a void or opening 218. The outer perimeter area 214 may be configured (e.g., sized, shaped, positioned) for securement to the patient's intact skull, and the inner perimeter area 216 may be configured for securement to the bone flap 104.

Optionally, the void or opening 218 surrounded by the inner perimeter area 216 may be customized for a particular procedure and/or patient. The void or opening 218 may be advantageous for lowering the weight of the device, providing access to the bone flap, and the like. Thus, it is contemplated that the opening 218 may be formed via cutting prior to initiation of the surgery (or during the surgery). The base plate 204 may include markings or other features to facilitate such cutting. In other embodiments, the opening 218 may be pre-formed and standard (perhaps with different available sizes). It is contemplated that the void or opening 218 may be absent from certain base plates, particularly where the bone flap is compromised such that additional support and covering by the base plate is necessary.

Figure 9:
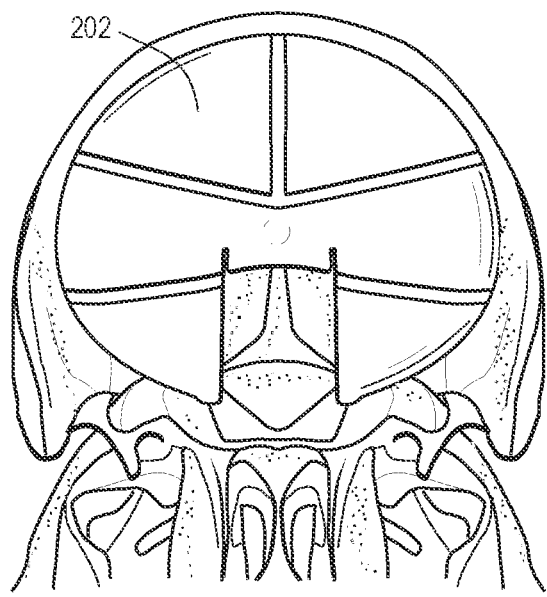
FIGS. 9-10 are illustrations showing an affixation device having topography features that are custom formed to a patient skull in accordance with certain aspects of the present disclosure.
Figure 10:
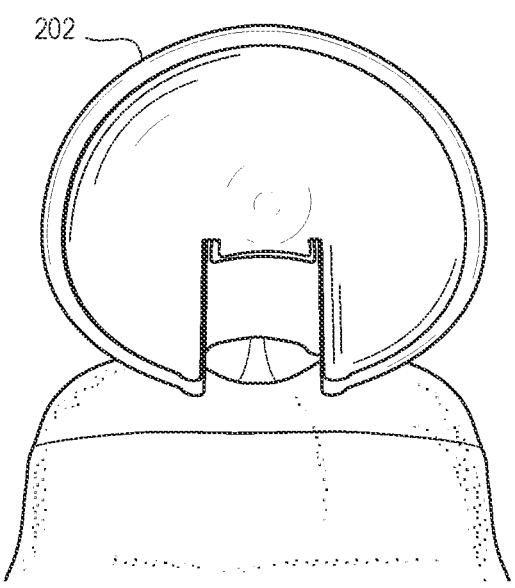
Figure 11:
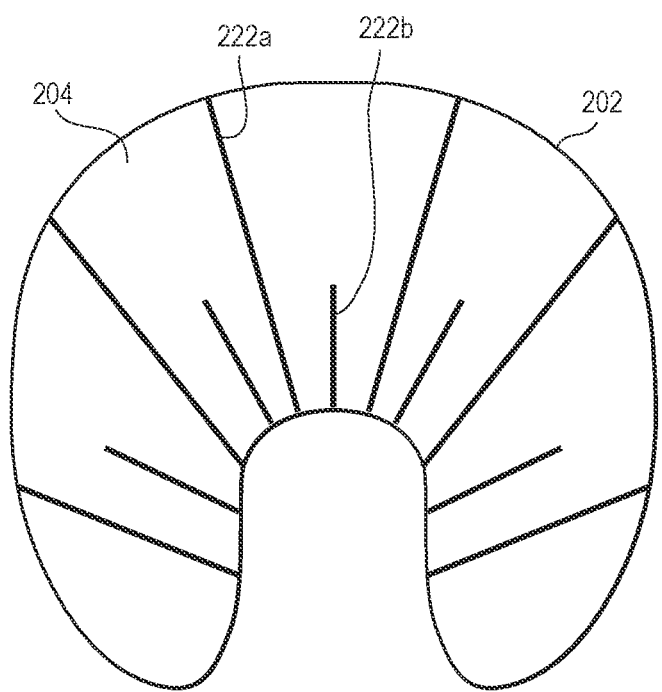
FIG. 11 is an illustration showing an affixation device having a set of flex lines that do not intersect in accordance with certain aspects of the present disclosure.

In some embodiments, the base plate 204 may generally curve or may be otherwise shaped for enhanced contact with the surgical site. As shown in FIGS. 6 and 9-10, the first side 208 of the base plate 204, which faces the patient, may have a concave surface 220 that generally mimics a corresponding convex shape of the exterior surface of the skull base. Advantageously, the natural contact area between the base plate 204 and the patient's skull may be significantly enhanced relative to other shapes.

Optionally the base plate 204 may have flexibility and compliance such that it can be manipulated into an appropriate shape. In some embodiments, (and as shown by FIGS. 7-11), a set of flex lines 222 or other flex points/areas may be included, which are designed to flex upon receipt of a force such that the general profile shape of the base plate 204 can be manipulated via human effort. The flex lines 222 may be formed with any suitable structure. For example, various flex lines via grooves within the material of the base plate 204, areas with different material properties (e.g., where a compliant material is located between relatively rigid zones, each zone having at least one screw hole or other fastener), etc. When the flex lines 222 are formed as grooves, it is contemplated that the grooves may be pre-cut or alternatively customized by the surgeon. In other examples, the entirety of the base plate 204 may be generally compliant and manipulatable such that distinct flex areas are unnecessary.

When flex lines 222 are included, they may have any suitable location and orientation on the base plate 204. In certain exemplary embodiments, the flex lines 222 (or at least a portion of them) may generally extend radially outward from an approximate centerpoint defined by the outer perimeter area 214. In FIGS. 7-9, for example, several of the flex lines 222 may converse at a primary flex point 224, which may be advantageous where the angle of concavity is desired to be greatest near the primary flex point 224 versus other areas of the base plate 204 (meaning the profile of the base plate is different in different locations, and in this embodiment, the ends 226 of the U-shaped base plate 204 may remain relatively flat). In a different arrangement shown in FIG. 11, the flex lines 222 do not intersect, and longer flex lines 222a generally alternate with shorter flex lines 222b that terminate prior to reaching the outer edge of the base plate. This embodiment may be advantageous for providing a relatively consistent curvature throughout the base plate (regardless of the level of concavity). Many other flex line or flex area arrangements are alternatively contemplated such that the base plate 204 is adapted for a particular surgical procedure.

In more complex embodiments, additional shaping of the base plate 204 may be used. For example, it is contemplated that the patient's skull topography may be scanned prior to initiation of the procedure, followed by customized shaping of the base plate's interior surface (perhaps including topography features and even spacing features) via a suitable manufacturing method, including but not limited to 3D printing. For example, it is contemplated that the embodiments of FIGS. 9-10, which have irregular surface properties matching the patient's skull, may be formed via 3D printing (or another method) for use only on the specific patient.

When removing the bone flap 104, a gap 106 may be formed that corresponds to the width of the surgeon's drill or other cutting tool (i.e., where the outer perimeter of the resulting bone flap 104 may be slightly smaller than the corresponding opening within the skull 102). Notably, the gap 106 may be horse-shoe shaped (e.g., see FIG. 2, where the bone flap extends to the bottom edge of the skull), may be continuous in a ring (e.g., see FIG. 3), or may be another suitable shape. To account for this gap 106 discussed above, one or more bone spacers 206 may be secured to the first side 208 of the base plate 204 such that, when deployed, the bone spacers 206 extend at least partially into the bone gap 106 between the bone flap 104 and the skull 102. The bone spacers 206 may generally include a tapered shape such that a cross-sectional area adjacent to the base plate 204 is greater than a cross-sectional area at the spacer's terminus (i.e., location farthest from the base plate 204), although this tapered shape is optional. In other words, the size of the spacers 206 may generally decrease as the spacers 206 extend away from the base plate 204. Advantageously, the tapered nature of the spacers 206 may make the insertion process easier on the surgeon and/or may create a natural tendency for the bone flap 104 to center itself within the skull's opening. In the depicted embodiment, the spacers 206 are shaped as frustums having rectangular cross-sections, but other suitable shapes are additionally or alternatively contemplated (and it is noted that different spacers may have different shapes). The spacers may also have any suitable size, and different-sized spacers may be selectable by the surgeon.

Any suitable number of spacers 206 may be included. E.g., in FIGS. 7-8, there are four (4) included spacers 206, but this number is used only as an example for purposes of illustration. Particularly when the spacers 206 are attachable and/or moveable (as discussed in more detail below), a surgeon may select a particular number of spacers 206, and locate them accordingly, depending on the needs of the specific patient and the surgeon's personal experiences and preferences.

In some embodiments, the positions of the spacers 206 may be customized in preparation for, or during, a specific surgical procedure. For example, since the bone flap is not always the same size from patient-to-patient, the spacers 206 may be selectively placed in appropriate locations for receipt by the bone gap on a case-by-case basis. Thus, the spacers 206 and the base plate 204 may be configured for customized placement and attachment of the spacers 206. For example, in some embodiments, the spacers 206 may include at least one male fastener 228 that is integral with the remainder of the spacer and is designed to extend at least partially through the thickness of the base plate 204. The base plate 204 may optionally include a corresponding female opening for receipt of the male fastener 228. Securement between the male fastener 228 and the base plate 204 may occur via friction fit (and additional friction-enhancing features, such as "push rivet" features or other radial-facing protrusions on the male fastener 228 and/or the female opening may be included).

Other structures and methods for securing the spacers 206 to the base plate 204 are additionally or alternatively contemplated. For example, the spacers 206 may be screwed (or otherwise secured via a different pin type) to the base plate 204, perhaps where a screw is introduced on the second side 210 of the base plate 204 and extends through the base plate 204 towards the spacers 206. In some embodiments, an adhesive may be used. In other embodiments, the one or more spacers 206 may be formed integrally with the base plate 204 (meaning the spacer(s) and base plate are formed with a common material and no post-processing attachment step is needed).

Like the base plate 204, the spacers 206 may be formed from a resorbable material. However, this is optional. The spacers 206 may be formed with a different material, particularly where the material characteristics desired are different from those desired within the base plate 204. In some embodiments, the spacers 206 may be formed of a compliant material (whether resorbable or not), which may be advantageous where the spacers 206 may need to (or are desired to) deform within the gap to enhance the device's fit and permanent placement.

While various embodiments have been described, it will be apparent to those of ordinary skill in the art that many more embodiments and implementations are possible. Accordingly, the embodiments described herein are examples, not the only possible embodiments and implementations.

Having described various aspects of the subject matter above, additional disclosure is provided below that may be consistent with the claims originally filed with this disclosure. In describing this additional subject matter, reference may be made to the previously described figures. Any of the following aspects may be combined, where compatible.

One general aspect includes an affixation device for a human skull. A base plate may include an outer area for securing to the skull and an inner area for securing to a bone flap removed from the skull. The affixation device also includes and at least one spacer located between the outer area and the inner area, where the at least one spacer extends from a first surface of the base plate, where the first surface facing the skull when the fixation device is in an installed state, and where the at least one spacer is configured to extend between the bone flap and the skull in the installed state.

In some embodiments, the base plate includes a u-shape having a void surrounded by the inner area, where the void is aligned with the bone flap when the affixation device is in the installed state.

The first surface of the base plate may include a concave shape for conforming to an outer skull surface of the skull.

The base plate may include a plurality of flex lines that are flexible relative to surrounding areas of the base plate. At least three flex lines of the plurality of flex lines may converge at a flex point. The flex lines extend radially away from a center area of the affixation device. The flex points may delineate a plurality of rigid zones of the base plate, where each rigid zone of the plurality of rigid zones includes is secured to at least one of the skull and the bone flap when the affixation device is in the installed state.

The base plate may include a plurality of holes for receiving bone screws.

The at least one spacer may include a first spacer with at least one tapered surface such that an apex of the first spacer is smaller than a base end of the spacer, where the base end of the spacer abuts the first surface of the base plate.

The at least one spacer may include a first spacer formed of a compliant material.

Another general aspect includes an affixation device for a human skull, which may include a base plate may include an outer area for securing to the skull and an inner area for securing to a bone flap removed from the skull. The base plate may have a u-shape having a void surrounded by the inner area, where the void is aligned with the bone flap when the affixation device is in the installed state.

The affixation device may include at least one spacer, where the at least one spacer extends from a first surface of the base plate, where the first surface facing the skull when the fixation device is in an installed state, and where the at least one spacer is configured to extend between the bone flap and the skull in the installed state.

The first surface of the base plate may include a concave shape for conforming to an outer skull surface of the skull.

The base plate may include a plurality of flex lines that are flexible relative to surrounding areas of the base plate. At least three flex lines of the plurality of flex lines may converge at a flex point. The flex lines may extend radially away from a center area of the affixation device. The flex points may delineate a plurality of rigid zones of the base plate, where each rigid zone of the plurality of rigid zones includes is secured to at least one of the skull and the bone flap when the affixation device is in the installed state.

The base plate may include a plurality of holes for receiving bone screws.

Another general aspect includes a method for constructing any of the aspects described above, along with a method for installing the same surgically.

We claim:

1. An affixation device for a human skull, comprising:
   a base plate comprising an outer area for securing to the skull and an inner area for securing to a bone flap removed from the skull, wherein a U-shaped boundary is located between the outer area and the inner area; and
   at least one spacer located between the outer area and the inner area, wherein the spacer separates the outer area from the inner area along the U-shaped boundary,
   wherein the at least one spacer extends from a first surface of the base plate,
   wherein the first surface faces the skull when the affixation device is in an installed state, and
   wherein the at least one spacer is configured to extend between the bone flap and the skull in the installed state.

2. The affixation device of claim 1, wherein the base plate includes a void surrounded by the inner area such that the inner area is located between the void and the outer area, wherein the void is aligned with the bone flap when the affixation device is in the installed state.

3. The affixation device of claim 1, wherein the first surface of the base plate includes a concave shape for conforming to an outer skull surface of the skull.

4. The affixation device of claim 1, wherein the base plate includes a plurality of flex lines that are flexible relative to surrounding areas of the base plate.

5. The affixation device of claim 4, wherein at least three flex lines of the plurality of flex lines converge at a flex point.

6. The affixation device of claim 4, wherein the flex lines extend radially away from a center area of the affixation device.

7. The affixation device of claim 4, wherein the flex lines delineate a plurality of rigid zones of the base plate, and wherein each rigid zone of the plurality of rigid zones is secured to at least one of the skull and the bone flap when the affixation device is in the installed state.

8. The affixation device of claim 1, wherein the base plate includes a plurality of holes for receiving bone screws.

9. The affixation device of claim 1, wherein the at least one spacer includes a first spacer with at least one tapered surface such that an apex of the first spacer is smaller than a base end of the spacer, and wherein the base end of the spacer abuts the first surface of the base plate.

10. The affixation device of claim 1, wherein the at least one spacer includes a first spacer formed of a compliant material.

11. An affixation device for a human skull, comprising:
a base plate comprising an outer area for securing to the skull and an inner area for securing to a bone flap removed from the skull,
wherein the base plate includes a U-shape having a void surrounded by the inner area, wherein the void is aligned with the bone flap when the affixation device is in an installed state; and
a spacer configured to secure to a first surface of the base plate, wherein the first surface is a skull-facing surface when the affixation device is in the installed state, wherein a position for the spacer is customizable to adjust a boundary location between the inner area and the outer area.

12. The affixation device of claim 11, wherein the spacer includes a male fastener configured for receipt into one of a plurality of female fasteners of the base plate based on a desired placement of the spacer.

13. The affixation device of claim 11, wherein the first surface of the base plate includes a concave shape for conforming to an outer skull surface of the skull.

14. The affixation device of claim 11, wherein the base plate includes a plurality of flex lines that are flexible relative to surrounding areas of the base plate.

15. The affixation device of claim 14, wherein at least three flex lines of the plurality of flex lines converge at a flex point.

16. The affixation device of claim 14, wherein the flex lines extend radially away from a center area of the affixation device.

17. The affixation device of claim 14, wherein the flex lines delineate a plurality of rigid zones of the base plate, and wherein each rigid zone of the plurality of rigid zones is secured to at least one of the skull and the bone flap when the affixation device is in the installed state.

18. The affixation device of claim 11, wherein the base plate includes a plurality of holes for receiving bone screws.

* * * * *